United States Patent [19]

Manzo

[11] Patent Number: 4,763,667
[45] Date of Patent: Aug. 16, 1988

[54] TISSUE-PENETRATING CATHETER DEVICE

[75] Inventor: Michael P. Manzo, Upton, Mass.

[73] Assignee: Microvasive, Inc., Milford, Mass.

[21] Appl. No.: 909,624

[22] Filed: Sep. 19, 1986

[51] Int. Cl.$^4$ ............................................. A61B 10/00
[52] U.S. Cl. .................................... 128/750; 128/752; 128/754; 604/164; 604/173
[58] Field of Search ............................... 128/749–750, 128/751–754, 756; 604/164–165, 173

[56] References Cited

U.S. PATENT DOCUMENTS

| 268,996 | 12/1882 | Brinkerhoff. | |
|---|---|---|---|
| 1,213,001 | 1/1917 | Philips. | |
| 3,330,268 | 7/1967 | Goldsmith | 128/753 |
| 3,470,867 | 10/1969 | Goldsmith | 128/753 |
| 3,538,916 | 11/1970 | Wiles et al. | |
| 4,222,380 | 9/1980 | Terayama. | |
| 4,230,123 | 10/1980 | Hawkins, Jr. | 128/753 X |
| 4,231,368 | 11/1980 | Becker. | |
| 4,243,048 | 1/1981 | Griffin | 128/754 X |
| 4,254,762 | 3/1981 | Yoon | 128/754 X |
| 4,258,722 | 3/1981 | Sessions et al. | 128/753 |
| 4,262,676 | 4/1981 | Jamshidi | 128/754 X |
| 4,333,459 | 6/1982 | Becker. | |

FOREIGN PATENT DOCUMENTS

| 143084 | 5/1920 | United Kingdom. | |
|---|---|---|---|
| 2126100 | 3/1984 | United Kingdom | 128/749 |

OTHER PUBLICATIONS

Commercial literature of Microvasive, Inc.

Primary Examiner—Kyle L. Howell
Assistant Examiner—Angela D. Sykes

[57] ABSTRACT

A tissue-penetrating catheter device for use within the body consists of: an outer catheter assembly including an outer catheter having distal and proximal ends, and a terminal member joined to the proximal end; an inner catheter assembly including an inner catheter extending within the outer catheter and having distal and proximal ends, and defining a conduit therethrough, a fluid connector at the proximal end for connecting the conduit to a fluid flow device, and a tissue-penetrating element, e.g., a needle, at the distal end sized to enter the distal end of the outer catheter. Also included are: structure for moving the inner catheter axially with respect to the outer catheter in a manner to move the needle axially between a protected position in which the tissue-penetrating means is disposed within the outer catheter and a projected position with the needle projecting beyond the outer catheter, exposed to enter tissue; and a pair of cooperating stop surfaces associated with respective portions of the catheter assemblies for limiting the distance of relative distal axial movement of the catheters. One of the stop surfaces is carried by a presettable, axially adjustable member capable of being selectably positioned along its catheter assembly to enable the physician to preselect the amount of projection of the needle from the outer catheter when the inner catheter assembly is moved to projected position.

8 Claims, 2 Drawing Sheets

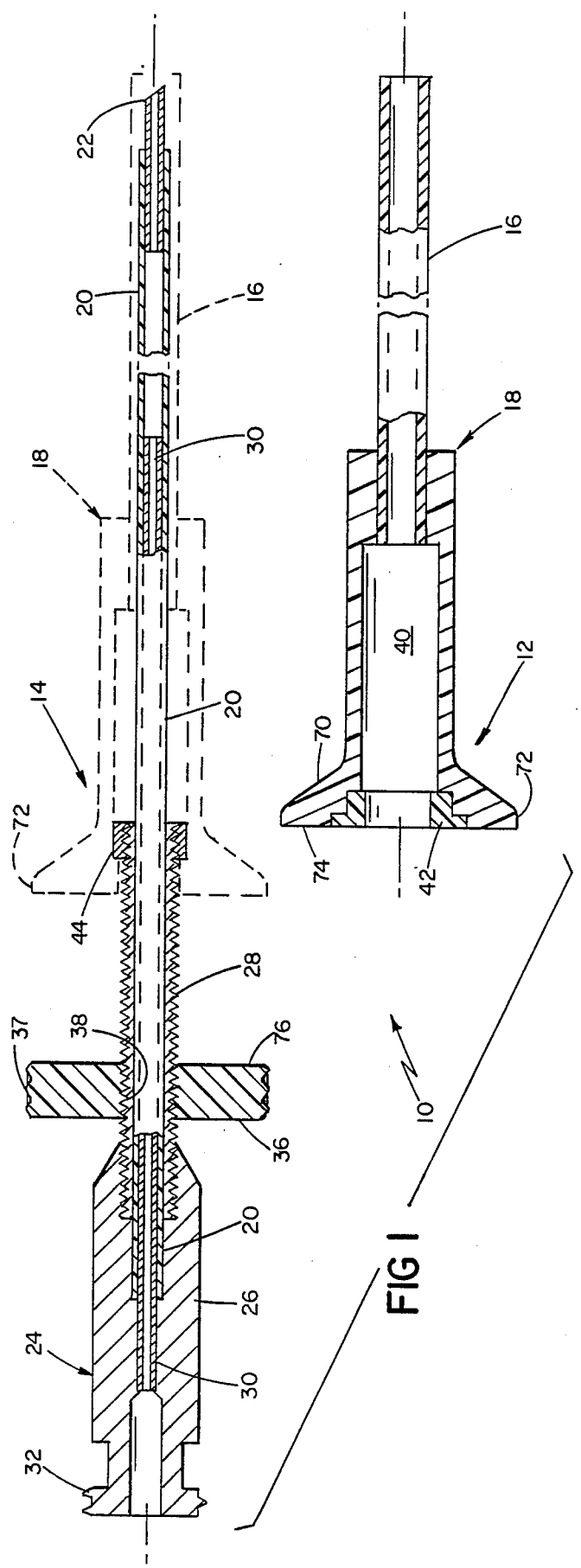
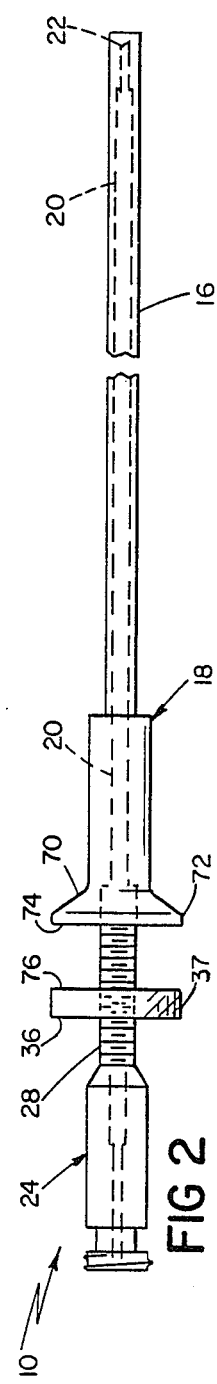
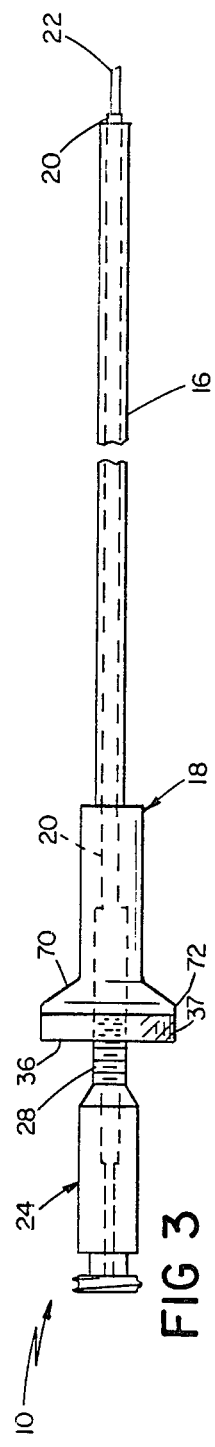
FIG 1
FIG 2
FIG 3

TISSUE-PENETRATING CATHETER DEVICE

The invention relates to tissue-penetrating catheter devices of the type capable of use within the body for remotely injecting fluid or removing tissue samples by suction, typically such devices being inserted through the working channel of an endoscope.

Such devices typically include an inner, conduit-forming catheter ending distally in a needle or other tissue-penetrating element, and an outer catheter, the inner and outer catheters being moveable axially with respect to each other, to move the tissue-penetrating element between a protected position within the outer catheter and a usually preset, projecting, tissue-penetrating position beyond the distal end of the outer catheter.

SUMMARY OF THE INVENTION

According to the invention, a tissue-penetrating catheter device for use within the body comprises: an outer catheter assembly comprising an outer catheter having a distal end and a proximal end, and a terminal member joined to the proximal end of the outer catheter, an inner catheter assembly comprising an inner catheter extending within the outer catheter and having a distal end and a proximal end, and defining a conduit therethrough, a fluid connector means at the proximal end of the inner catheter for connecting the conduit to means for producing fluid flow, and tissue-penetrating means at the distal end of the inner catheter sized to enter the distal end of the outer catheter, means for moving the inner catheter axially with respect to the outer catheter in a manner to move the tissue-penetrating means axially between a protected position in which the tissue-penetrating means is disposed within the outer catheter and a projected position in which the tissue-penetrating means projects beyond the outer catheter, exposed to enter tissue, and a pair of cooperating stop surfaces associated with respective portions of the inner and outer catheter assemblies for limiting the distance of distal axial movement of the inner catheter relative to the outer catheter, one of the stop surfaces being carried by a presettable, axially adjustable member capable of being selectably positioned along its catheter assembly to enable the physician to preselect the amount of projection of the tissue-penetrating means from the outer catheter when the inner catheter assembly is moved to the projected position.

In the preferred embodiments, the tissue penetrating means is a needle joined to the distal end of the inner catheter; and the sleeve and terminates proximally in an enlarged surface adapted device is sized and constructed for introduction into the body through a working channel of a flexible endoscope; the terminal member has the form of a to rest between fingers of a physician to stabilize the outer catheter assembly from distal axial motion, the proximal end of the terminal member forming a relatively stationary, first of the stop surfaces, and the fluid connector means comprises an elongated distal shaft sized and constructed to telescope into the sleeve-form terminal member, the shaft defining a range of selectable positions for the presettable, axially adjustable member, the adjustable member defining a relatively adjustable, second of the stop surfaces, preferably the elongated distal shaft is threaded, and the axially adjustable member is in the form of a nut adjustable by rotation about the shaft; and the device further comprises a second pair of cooperating stop surfaces associated with respective portions of the inner and outer catheter assemblies for limiting the distance of proximal axial movement of the inner catheter relative to the outer catheter; the characteristic thermal expansion of the inner catheter is different from the characteristic thermal expansion of the outer catheter.

These and other objectives and features of the invention will be understood from the following description of a preferred embodiment; and from claims.

BRIEF DESCRIPTION OF THE DRAWINGS

We first briefly describe the drawings.

Drawings

FIG. 1 is a side section view of the separate assemblies of the elongated tissue-penetrating catheter device of the invention;

FIGS. 2 and 3 are side views of the device of the invention, with the tissue-penetrating needle respectively withdrawn and projected; and FIG. 4 is a somewhat diagrammatic view of the elongated catheter device of the invention in the form of a sclerotherapy needle in use through a flexible endoscope for treatment of esophogeal varices, while

DESCRIPTION OF THE PREFERRED EMBODIMENTS

Figure 4:
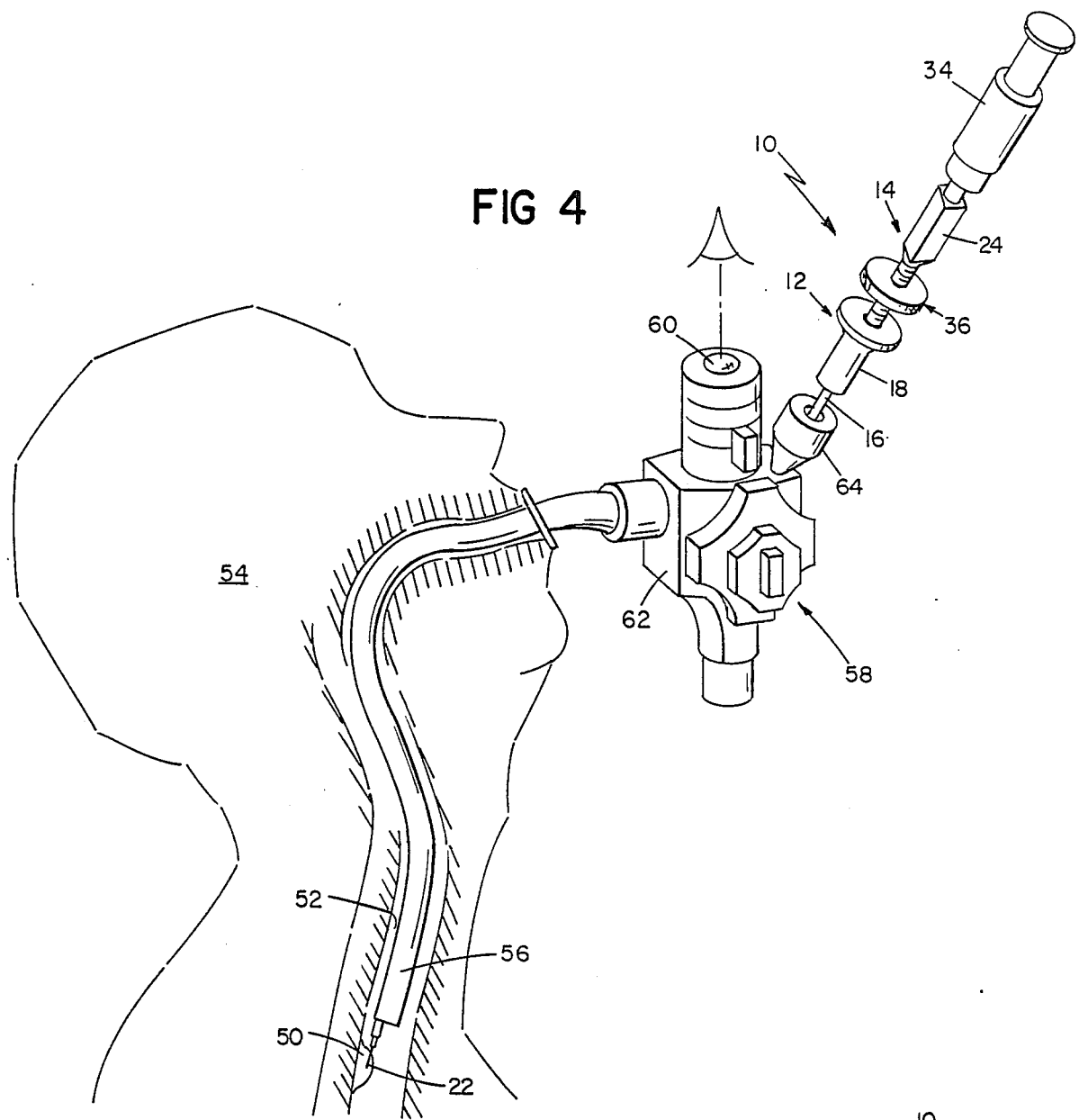

The elongated catheter device 10 of the invention has an outer catheter assembly 12 and an inner catheter assembly 14. The outer catheter assembly consists of an elongated, e.g., about 200 cm, catheter 16 of outer diameter sized to pass through the working channel of a flexible endoscope, e.g., 1.8 mm, and a terminal member 18 joined to the proximal end of the outer catheter. The inner catheter assembly consists of an elongated catheter 20 of outer diameter selected to allow movement of the inner catheter axially within the bore of the outer catheter, a tissue-penetrating element 22, e.g., a needle, joined to distal end of the inner catheter, and, at the proximal end of the inner catheter, a fluid connector 24 having a body 26 and a distal threaded shaft 28. The inner catheter extends through the connector shaft and into the body and, within the proximal portion of the inner catheter, there is disposed a stiffener 30 of metal hypodermic tubing extending from the connector body, through the shaft and distally within the inner catheter for a length sufficient to cause the distal end of the stiffener to extend distally of the terminal member when the device is assembled. The proximal end 32 of the fluid connector has the form of a female luer constructed for threaded connection to a means, e.g., a syringe 34, as shown in FIG. 4, for producing fluid flow through the conduit defined by the connector body, the stiffener, the inner catheter and distal needle.

The device further includes a large diameter adjustment member 36, having a knurled outer surface 37 and a center bore 38 sized for threaded engagement about shaft 28, the axial position of the adjustment member along the shaft being adjusted by rotation of the member about the shaft.

When assembled, the inner catheter 20 extends within the outer catheter 16, and the shaft 28, with adjustment member 36 positioned thereupon, extends into the center bore 40 of terminal member 18 through retaining ring 42 which is snap fit into the proximal end of bore 40. The distal end of shaft 28 is of a diameter greater than the diameter of ring 42, e.g., by virtue of a sleeve 44 affixed about the shaft, engagement of the sleeve with the ring limiting the distance of proximal movement of the inner catheter relative to the outer catheter, thereby limiting the maximum distance that the tissue-penetrating member can be drawn proximally from the distal end of the outer catheter and also limiting the length of outer catheter unsupported by the inner catheter, which, disposed therewithin, in part, serves to restrict kinking.

Referring now to FIGS. 2, 3 and 4, the device 10 of the invention is shown in the form of a sclerotherapy needle for use in treatment of varices 50 in the esophagus 52 of a patient 54.

The physician inspects the device by grasping the terminal member between fingers, with the fingers resting against the distal surface 70 of proximal flange 72, and urges the adjustable member 36 toward the terminal member until engagement of opposed terminal member surface 74 and adjustment member surface 76 limits further distal axial movement of the inner catheter relative outer catheter. The physician determines if he has the desired length of projection of the needle beyond the distal end of the outer catheter. If not, the length of projection is adjusted, distally or proximally, by rotation of the adjustment member about the shaft.

When the desired amount of projection is achieved, the physician draws inner catheter assembly 14 proximally of the outer catheter assembly (FIG. 2), preferably to the position of engagement of the sleeve 44 with ring 42. In this position, the tissue-penetrating needle 22 is withdrawn into the distal end of the outer catheter 16 to prevent engagement of the distal needle with the wall of the endoscope working channel, to the possible damage of either or both. The engagement of the sleeve and ring also serves to limit the distance by which the needle is withdrawn into the outer catheter to avoid an unnecessary length of unsupported outer catheter at the distal tip which could result in kinking, or penetration of the needle through the outer catheter wall, especially when the scope extends about small radius bends.

The physician introduces the distal end portion 56 of flexible endoscope 58 through the mouth of the patent, and, viewing through the lens 60 of the endoscope handpiece 62, he steers the distal end of the scope until he observes a varice on the esophagus wall.

The distal end of the sclerotherapy needle 22 of the invention is then introduced through the endoscope valve 64 and fed through the working channel of the scope until the distal end of the device extends from the distal end of the scope.

Figure 4A:
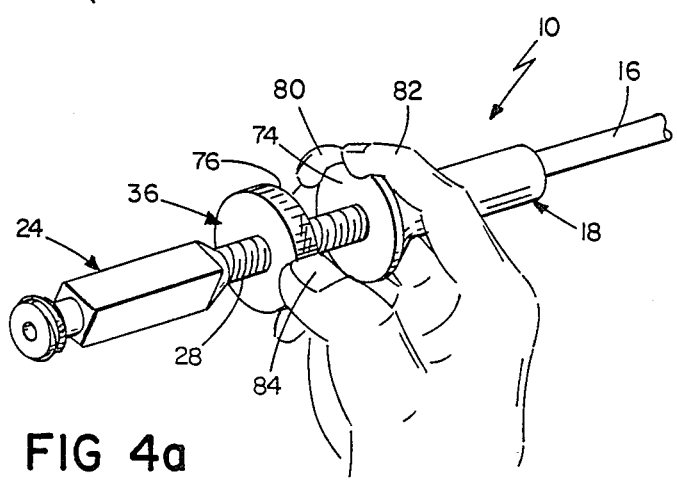
FIG. 4a is a similar view of the device being operated by a physician.

Referring to FIG. 4a, the physician grasps the terminal member 18 between fingers 80, 82 and draws opposed surfaces 74, 76 of the adjustment member and terminal member together until engaged, whereupon the needle 22 is extended to the predetermined limit. This operation can be performed using one hand only, with thumb 84 urging the adjustment member 36 distally, leaving the physician's other hand free. The needle is then inserted into the varice under visual observation through the endoscope, and fluid is injected using the syringe 34. Preferably, the inner and outer catheters are of contrasting colors, e.g., black and white, to allow the physician to easily distinguish them within the body. The physician can then withdraw the needle back into the outer catheter and repeat the procedure at other sites.

If the physician wishes to change or adjust the length of needle extension, e.g., if the materials of the inner and outer catheter exhibit different degrees of thermal expansion within the body, this is simply accomplished while the device remains in position within the working channel of the endoscope by rotation of the adjustment member 36 about the shaft 28 to move the member in the desired direction. (Preferably, the member fits snuggly on the shaft so that accidental rotation is avoided.) Again, this can be done using one hand only.

Other embodiments are within the following claims, for example, the device may be used other than through the working channel of an endoscope, and other medical procedures are contemplated, e.g., treatment of ulcers by injection, tattooing of surgical sites in the colon for later identification, or biopsy of tumors or other tissue by applying suction through the device. Also, the terminal member and retaining ring and also the connector body, shaft and sleeve may be formed integrally, e.g. of modified acrylic, by injection molding about the respective catheters.

What is claimed is:

1. A tissue-penetrating catheter device for use within the body, comprising:

an outer catheter assembly comprising an outer elongated, flexible outer catheter having a distal end and a proximal end, and a terminal member joined to the proximal end of said outer catheter, said terminal member having the form of a sleeve and terminating proximally in an enlarged surface adapted to rest between fingers of a physician to stabilize said outer catheter assembly from distal axial motion, an inner catheter assembly comprising an elongated, flexible inner catheter extending within said outer catheter and having a distal end and a proximal end, and defining a flexible conduit therethrough, a fluid connector means at the proximal end of said inner catheter for connecting said conduit to means for producing fluid flow, said fluid connector means comprising an elongated distal shaft sized and constructed to telescope into the sleeve-form terminal member, and tissue-penetrating means at the distal end of said elongated, flexible inner catheter sized to enter the distal end of said elongated, flexible outer catheter, means for moving said inner catheter axially with respect to said outer catheter in a manner to move said tissue-penetrating means axially between a protected position in which said tissue-penetrating means is disposed within said outer catheter and a projected position in which said tissue-penetrating means projects beyond said outer catheter, exposed to enter tissue, a pair of cooperating stop surfaces associated with respective portions of said inner and outer catheter assemblies for limiting the distance of distal axial movement of said inner catheter relative to said outer catheter, the proximal end of said terminal member forming a relatively stationary, first of said stop surfaces, and a second of said stop surfaces being carried by a presettable, axially adjustable member capable of being selectably positioned along said shaft to enable the physician to preselect the amount of projection of said tissue-penetrating means from said outer catheter when said inner catheter assembly is moved to said projected position, said shaft defining a range of selectable positions for said presettable, axially adjustable member.

2. The tissue-penetrating catheter device of claim 1 wherein said elongated distal shaft is threaded, and said axially adjustable member is in the form of a nut adjustable by rotation about said shaft.

3. The tissue-penetrating catheter device of claim 1 further comprising a second pair of cooperating stop surfaces associated with respective portions of said inner and outer catheter assemblies for limiting the distance of proximal axial movement of said inner catheter relative to said outer catheter.

4. The tissue penetrating catheter device of claim 1 wherein the characteristic thermal expansion of said inner catheter is different from the characteristic thermal expansion of said outer catheter.

5. A tissue-penetrating catheter device in the form of an adjustable endoscopic needle for use within the body, comprising:

an outer catheter assembly comprising an elongated, flexible outer catheter having a distal end and a proximal end, and a terminal member joined to the proximal end of said outer catheter, said terminal member having the form of a sleeve and terminating proximally in an enlarged surface adapted to rest between fingers of a physician to stabilize said outer catheter assembly from distal axial motion, an inner catheter assembly comprising an elongated, flexible inner catheter extending within said outer catheter and having a distal end and a proximal end, and defining a flexible conduit therethrough, a fluid connector means at the proximal end of said inner catheter for connecting said conduit to means for producing fluid flow, said fluid connector means comprising an elongated distal shaft sized and constructed to telescope into the sleeve-form terminal member, and a needle joined to the distal end of said elongated, flexible inner catheter sized to enter the distal end of said elongated, flexible outer catheter, means for moving said inner catheter axially with respect to said outer catheter in a manner to move said tissue-penetrating means axially between a protected position in which said tissue-penetrating means is disposed within said outer catheter and a projected position in which said tissue-penetrating means projects beyond said outer catheter, exposed to enter tissue, a pair of cooperating stop surfaces associated with respective portions of said inner and outer catheter assemblies for limiting the distance of distal axial movement of said inner catheter relative to said outer catheter, the proximal end of said terminal member forming a relatively stationary, first of said stop surfaces, and a second of said stop surfaces being carried by a presettable, axially adjustable member capable of being selectably positioned along said shaft to enable the physician to preselect the amount of projection of said tissue-penetrating means from said outer catheter when said inner catheter assembly is moved to said projected position, said shaft defining a range of selectable positions for said presettable, axially adjustable member, whereby said device is sized and constructed for introduction into the body through a working channel of a flexible endoscope.

6. The adjustable endoscopic needle device of claim 5 wherein said elongated distal shaft is threaded, and said axially adjustable member is in the form of a nut adjustable by rotation about said shaft.

7. The adjustable endoscopic needle device of claim 5 further comprising a second pair of cooperating stop surfaces associated with respective portions of said inner and outer catheter assemblies for limiting the distance of proximal axial movement of said inner catheter relative to said outer catheter.

8. The adjustable endoscopic needle device of claim 5 wherein the characteristic thermal expansion of said inner catheter is different from the characteristic thermal expansion of said outer catheter.

* * * * *

UNITED STATES PATENT AND TRADEMARK OFFICE
CERTIFICATE OF CORRECTION

PATENT NO. : 4,763,667
DATED : August 16, 1988
INVENTOR(S) : Michael P. Manzo

It is certified that error appears in the above-identified patent and that said Letters Patent is hereby corrected as shown below:

Column 1, lines 52-53, change the semicolon after "catheter" to a comma and delete "sleeve and terminates proximally in an enlarged surface adapted".

Column 1, line 56, after "has the form of a", insert --sleeve and terminates proximally in an enlarged surface adapted--.

Signed and Sealed this

Twenty-eighth Day of March, 1989

Attest:

DONALD J. QUIGG

Attesting Officer

Commissioner of Patents and Trademarks